United States Patent [19]
Laux

[11] Patent Number: 5,888,010
[45] Date of Patent: Mar. 30, 1999

[54] DISPENSER FOR A SHEET-LIKE CLEANING AND DENTAL-CARE FORMULATION

[75] Inventor: Wolfgang Laux, Diez, Germany

[73] Assignee: LTS Lohmann Therapie-Systeme GmbH, Neuwied, Germany

[21] Appl. No.: 817,203

[22] PCT Filed: Oct. 10, 1995

[86] PCT No.: PCT/EP95/03978

§ 371 Date: Apr. 11, 1997

§ 102(e) Date: Apr. 11, 1997

[87] PCT Pub. No.: WO96/11599

PCT Pub. Date: Apr. 25, 1996

[30] Foreign Application Priority Data

Oct. 12, 1994 [DE] Germany .......................... 44 36 387.7

[51] Int. Cl.[6] ....................................................... A46B 11/00
[52] U.S. Cl. ........................................... 401/268; 401/282

[58] Field of Search ..................................... 401/268, 269, 401/282, 289, 140, 143, 147

[56] References Cited

U.S. PATENT DOCUMENTS 4,963,046  10/1990  Eguchi ..................................... 401/160
5,490,530   2/1996  Snowden ................................. 132/311

FOREIGN PATENT DOCUMENTS

WO 92/05721  4/1992  WIPO ..................................... 401/268

*Primary Examiner*—David J. Walczak
*Attorney, Agent, or Firm*—Wenderoth, Lind & Ponack, L.L.P.

[57] ABSTRACT

A dispenser for a cleaning and dental-care formulation which is present in solid form as a sheet (1) and is provided in conjunction with a toothbrush (10) for oral and dental hygiene is characterized in that the dispenser and the toothbrush (10) together are designed as a functional unit (20).

6 Claims, 1 Drawing Sheet

DISPENSER FOR A SHEET-LIKE CLEANING AND DENTAL-CARE FORMULATION

The invention relates to a dispenser for a cleaning and dental-care formulation which is present in solid form as a sheet and is provided in conjunction with a toothbrush for oral and dental hygiene.

BACKGROUND OF THE INVENTION

Such a cleaning and dental-care formulation in solid form is also known as a "cleaning wafer".

Toothbrushes are generally known means for cleaning teeth manually. For the cleaning procedure, an amount of toothpaste is usually applied, from a dispenser tube, directly to the brush and cleaning is carried out therewith. Cleaning means in the form of powders or in granular form are also known, these cleaning means sticking to the ends of the bristles, once the previously moistened toothbrush has been dipped therein, and being applied to the teeth by the toothbrush in this way.

Recently, sheet-like teeth-cleaning formulations in solid form, known as "dental-care wafers", which are intended to replace the function of toothpaste have been developed. Such wafers may be stored either as pre-cut individual formulations or as a sheet, preferably in the form of a roll. In any case, a satisfactory technical solution for the usage of these novel sheets or sheet sections, that is to say for the application thereof to the head of the toothbrush, have still not been found or made commercially available. This is because the person using these sheets or sheet sections has to avoid using his or her fingers for applying them to the toothbrush, because it is generally assumed that teeth cleaning is part of a daily body-care routine, in which case one's fingers, if not exactly wet, are at least moist, as a result of which the wafers partly dissolve and either stick to the fingers or disintegrate. There is thus an urgent need to develop a dispenser which is intended for the convenient and ergonomically favourable application of dental-care wafers and takes account of the practical requirements of simple and straightforward storage as well as the application of sheet-like dental-care formulations.

DESCRIPTION OF THE INVENTION

The object of the invention is to specify a dispenser for a cleaning and dental-care formulation which is present in solid form as a sheet and is provided in conjunction with a toothbrush for oral and dental hygiene, this dispenser permitting, in a simple and uncomplicated manner, application and storage of a dental-care wafer without the latter coming into contact with one's fingers.

The object is achieved by the invention in that the dispenser and the toothbrush together are designed as a functional unit.

One configuration provides that the sheet is stored in the form of a roll in the handle of the toothbrush.

For this purpose, it is also provided that the toothbrush has a receiving space for the storage roll.

Further advantageous configurations of the invention are provided in accordance with the disclosure.

BRIEF DESCRIPTION OF THE DRAWING

The FIGURE of drawing depicts an embodiment of the invention.

An exemplary embodiment of the invention is presented hereinbelow, with reference to a drawing, it being possible for further advantageous configurations to be gathered from the drawing.

Figure 1:
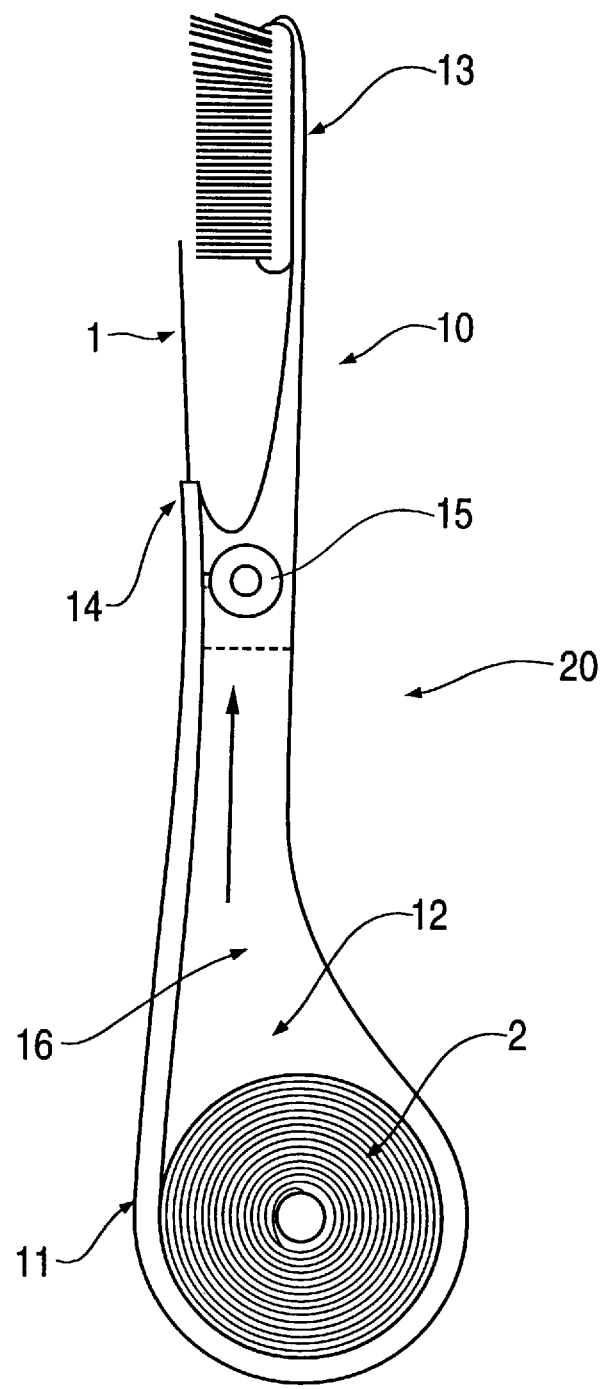

The FIGURE shows a toothbrush 10 which is designed as a functional unit 20 together with a dispenser for a cleaning and dental-care formulation which is present in solid form as a sheet 1 and is provided in conjunction with the toothbrush 10 for oral and dental hygiene.

The sheet 1 is stored in the form of a roll 2 in the handle 11 of the toothbrush 10, for which purpose a receiving space 12 for the storage roll 2 is formed on the handle 11 of the toothbrush 10.

It is fundamental to the invention that, at a location in the vicinity of the head 13 of the toothbrush 10, the receiving space 12 has an outlet orifice 14, directed towards the head 13 of the toothbrush 10, for the sheet 1. Furthermore, a preferably hand-actuable advancement device 15 for the sheet 1 is arranged at said location.

In a further embodiment of the functional unit 20, comprising toothbrush 10 and dispenser, it is provided that the receiving space 12 has a laterally arranged snap-action cover 16 which extends as far as the advancement device 15. When said cover is open, a new roll 2 can be inserted and threaded through the outlet orifice. In order to make it possible for the user to monitor the supply of wafer-containing sheet, it is also provided that the snap-action cover 16 consists of transparent plastic.

The advancement device 15 has a shaft which is mounted in the handle 11 of the toothbrush 10 and has a drive wheel which is arranged in the interior of the handle 11 and is made of soft resilient material. The shaft projects out of the handle casing, through a bearing bore, by way of a grip end and can thus easily be rotated by one's fingers, as a result of which, with an appropriate direction of rotation, the sheet 1, guided between the wheel and the inner wall of the toothbrush handle 11, is pushed out of the outlet orifice 14, by means of the shaft, in the direction of the advancement arrow. It is not necessary here for the wafer or the sheet 1 to come into contact with one's fingers.

In order to be able to apply wafer sections of predetermined length to the brush head 13, it is possible, in a further configuration of the sheet strip 1, for a transversely running line of weakness to be stamped in the sheet at certain intervals, this line of weakness then making it possible for a sheet section 1 of predetermined length to be broken off without difficulty.

The dispenser is uncomplicated, practical to handle and permits straightforward application of sheet-like cleaning and dental-care formulations in conjunction with a toothbrush.

I claim:

1. A toothbrush comprising:
    a bristle head including bristles having free bristle ends;
    a toothbrush handle connected to said bristle head, said toothbrush handle defining a wafer sheet receiving space and an outlet orifice communicating with said wafer sheet receiving space; and
    a hand-actuable advancement device for advancing a cleaning and dental-care formulation in the form of a solid wafer sheet toward said bristle head, said hand-actuable advancement device and said outlet orifice being positioned so as to deliver the solid wafer sheet from said wafer sheet receiving space to an area above said free ends of said bristles.

2. A toothbrush as claimed in claim 1, further comprising a roll of cleaning and dental-care formulation in the form of a solid wafer sheet provided in said wafer sheet receiving space.

3. A toothbrush as claimed in claim 1, wherein the advancement device is located at the end of the receiving space facing the bristle head.

4. A toothbrush as claimed in claim 1, wherein the receiving space has a laterally arranged snap-action cover which extends as far as the advancement device.

5. A toothbrush as claimed in claim 4, wherein the snap-action cover is transparent plastic.

6. A toothbrush according to one of claims 1, 2, 3, 4 or 5, wherein the advancement device has a shaft mounted in the said handle and a drive wheel mounted in the handle and connected to said shaft, said drive wheel being a soft elastic material and the shaft projecting out of the handle to provide a grip end.

\* \* \* \* \*